United States Patent
Mason (10) Patent No.: US 12,141,425 B2
(45) Date of Patent: Nov. 12, 2024

(54) ALERT RULE SYSTEM AND METHOD FOR UPDATING ALERT RULES

(71) Applicant: Myriad Women's Health, Inc., South San Francisco, CA (US)

(72) Inventor: Christopher John Mason, Portland, OR (US)

(73) Assignee: Myriad Women's Health, Inc., South San Francisco, CA (US)

(*) Notice: Subject to any disclaimer, the term of this patent is extended or adjusted under 35 U.S.C. 154(b) by 401 days.

(21) Appl. No.: 16/022,318

(22) Filed: Jun. 28, 2018

(65) Prior Publication Data
US 2019/0004692 A1    Jan. 3, 2019

Related U.S. Application Data

(60) Provisional application No. 62/526,506, filed on Jun. 29, 2017.

(51) Int. Cl.
| | |
|---|---|
| *G06F 3/04847* | (2022.01) |
| *G06F 3/0482* | (2013.01) |
| *G06Q 30/0283* | (2023.01) |
| *G08B 29/22* | (2006.01) |
| *G16H 80/00* | (2018.01) |

(52) U.S. Cl.
CPC ........ *G06F 3/04847* (2013.01); *G06F 3/0482* (2013.01); *G06Q 30/0283* (2013.01); *G08B 29/22* (2013.01); *G16H 80/00* (2018.01)

(58) Field of Classification Search
CPC ... G06F 3/04847; G06F 3/0482; G08B 29/22; G06Q 30/0283; G16H 80/00

USPC ........................................................ 715/751
See application file for complete search history.

(56) References Cited

U.S. PATENT DOCUMENTS

| | | | | |
|---|---|---|---|---|
| 8,310,361 | B1* | 11/2012 | Stout | G06F 16/29 340/539.2 |
| 8,725,527 | B1* | 5/2014 | Kahn | G06Q 50/22 705/2 |
| 2004/0073558 | A1 | 4/2004 | Schrijvers | |
| 2004/0081310 | A1* | 4/2004 | Lueckhoff | H04M 3/5191 379/265.09 |
| 2005/0276262 | A1* | 12/2005 | Schuba | H04L 47/20 709/200 |

(Continued)

OTHER PUBLICATIONS

International Search Report and Written Opinion issued in PCT/US2018/040095 on Aug. 31, 2018 (4 pages).

*Primary Examiner* — Matthew Ell
*Assistant Examiner* — Conrad R Pack
(74) *Attorney, Agent, or Firm* — Foley & Lardner LLP (57) ABSTRACT

According to one aspect, systems and processes for updating an alert rule are provided. In an exemplary process, one or more alert rules are displayed. A first user selection of a displayed alert rule is received, and in response, an alert modification interface corresponding to the selected alert rule is displayed. The alert modification interface may include one or more conditions for triggering a communication of an alert to an entity. At least one additional user selection indicative of a change to the one or more displayed conditions is received, where the conditions are for triggering the communication of an alert to an entity. In response to receiving the at least one additional user selection, the selected alert rule is updated.

19 Claims, 6 Drawing Sheets

(56) References Cited

U.S. PATENT DOCUMENTS

| | | | |
|---|---|---|---|
| 2007/0174092 A1* | 7/2007 | Lara | G16H 20/10 |
| | | | 434/262 |
| 2007/0271119 A1* | 11/2007 | Boerger | G06Q 40/00 |
| | | | 705/2 |
| 2008/0010086 A1* | 1/2008 | Skelly | G06Q 10/10 |
| | | | 705/2 |
| 2008/0058773 A1* | 3/2008 | John | A61N 1/37235 |
| | | | 604/891.1 |
| 2008/0143548 A1 | 6/2008 | Grimmelmann | |
| 2009/0094055 A1* | 4/2009 | Gage, Jr. | G16H 10/60 |
| | | | 705/400 |
| 2009/0216558 A1* | 8/2009 | Reisman | G16H 50/30 |
| | | | 705/3 |
| 2011/0071854 A1* | 3/2011 | Medeiros | G06Q 10/10 |
| | | | 707/769 |
| 2011/0199214 A1* | 8/2011 | Gawlick | A61B 5/0008 |
| | | | 340/573.1 |
| 2012/0056746 A1* | 3/2012 | Kaigler | A61B 5/0022 |
| | | | 340/573.1 |
| 2012/0280811 A1 | 11/2012 | Mckalip | |
| 2013/0096937 A1* | 4/2013 | Campbell | G06Q 10/10 |
| | | | 705/2 |
| 2013/0191157 A1* | 7/2013 | Eiden | G16H 10/60 |
| | | | 705/3 |
| 2013/0191647 A1* | 7/2013 | Ferrara, Jr. | G16H 10/60 |
| | | | 713/186 |
| 2013/0290037 A1* | 10/2013 | Hu | G06Q 40/08 |
| | | | 705/4 |
| 2014/0047323 A1* | 2/2014 | Bourke | G06F 9/542 |
| | | | 715/234 |
| 2014/0236614 A1* | 8/2014 | Whittier | G06Q 10/10 |
| | | | 705/2 |
| 2014/0257047 A1* | 9/2014 | Sillay | H04L 63/10 |
| | | | 600/595 |
| 2015/0019235 A1* | 1/2015 | Roychowdhury | G06Q 30/0627 |
| | | | 705/2 |
| 2015/0348398 A1 | 12/2015 | Williamson | |
| 2015/0363555 A1* | 12/2015 | Studsrud | G16H 40/20 |
| | | | 705/2 |
| 2016/0034571 A1* | 2/2016 | Setayesh | G06F 16/353 |
| | | | 707/738 |
| 2016/0350501 A1* | 12/2016 | Rothschild | G06Q 30/04 |
| 2017/0116373 A1* | 4/2017 | Ginsburg | G16H 10/40 |
| 2018/0122499 A1* | 5/2018 | Austin | G16H 10/60 |

\* cited by examiner

FIG. 1

| | ID 208 | Description 202 | Priority 203 | Active 204 | Rule summary | Add alerts 206 | Remove alerts 207 |
|---|---|---|---|---|---|---|---|
| 201a | 6 | Bad Patient Info | 4 | ✓ | - Has Bad Patient Info: True<br>- Has Order: True | - bad-patient-info | - prior-auth-text<br>- pre-test-counseling-text<br>- low-confidence-text |
| 201b | 15 | Prior Auth Required ABC Provider ICS | 1 | ✓ | - Product: Inherited Cancer Screen<br>- Insurance Payer: Aetna<br>- Needs Prior Auth: True | - prior-auth-text<br>- prior-auth-required-abcprovider-ics | - prior-auth-required |

ALERT RULE SYSTEM AND METHOD FOR UPDATING ALERT RULES

CROSS-REFERENCE TO RELATED APPLICATIONS

This application claims the benefit of U.S. Provisional Application No. 62/526,506, filed on Jun. 29, 2017, the entire disclosure of which is incorporated herein by reference in its entirety for all intended purposes.

FIELD

The following disclosure relates generally to an alert rule system and method for updating alert rules and triggering user notifications.

BACKGROUND

Facilitating communication of important information between entities typically requires significant organization and optimization of information, especially in the case when large quantities of data and computations are involved. Current platforms for communicating relevant information between entities, such as communicating an alert from a service provider to a service consumer, must routinely take into account vast amounts of information and constraints. At the same time, such systems must deliver the information in a concise, accurate, and legal manner. For example, calculating medical expenses and providing estimates of such expenses is often complicated, and patients are typically unaware of the various factors that have an impact on the cost of a given procedure. Moreover, current platforms for communicating such information are routinely associated with poor user experience, inadequate administrator customization, and lack of transparency in the information provided. Therefore, an improved alert rule system and method for updating alert rules is desired.

SUMMARY

According to one aspect of the present disclosure, a computer-implemented method of updating an alert rule is provided. In one embodiment, the method comprises: displaying, on a display, one or more alert rules; receiving a first user selection of a displayed alert rule; in response to receiving the user selection, displaying, on the display, an alert modification interface corresponding to the selected alert rule, wherein the alert modification interface includes one or more conditions for triggering a communication of an alert to an entity; receiving at least one additional user selection indicative of a change to the one or more displayed conditions for triggering the communication of an alert to an entity; and in response to receiving the at least one additional user selection, updating the selected alert rule.

In some embodiments, the alert modification interface further comprises at least one variable element configured to permit a user to modify information provided in the communication of an alert to an entity. In some embodiments, receiving at least one additional user selection indicative of a change to the one or more displayed conditions further comprises: receiving at least one property associated with a value; and generating the value within the communication of an alert to an entity. In some embodiments, the method further comprises: determining whether a calculation request matches the one or more conditions for triggering the communication, wherein in response to a determination that a calculation request matches the one or more conditions for triggering the communication, including the alert in the communication to the entity; and in response to a determination that a calculation request does not match the one or more conditions for triggering the communication, forgoing including the alert in the communication to the entity. In some embodiments, at least one alert rule of the one or more alert rules is associated with a priority level with respect to the one or more alert rules. In some embodiments, the entity is a patient and the communication is associated with health care information. In some embodiments, displaying one or more alert rules further comprises: displaying, on the display, a preview of a communication of an alert to an entity, wherein the preview of a communication of alert to an entity corresponds to a currently selected alert rule.

In some embodiments, the present invention includes a non-transitory computer readable storage medium having instructions stored thereon, the instructions, when executed by one or more processors, cause the processors to perform operations comprising: displaying, on a display, one or more alert rules; receiving a first user selection of a displayed alert rule; in response to receiving the user selection, displaying, on the display, an alert modification interface corresponding to the selected alert rule, wherein the alert modification interface includes one or more conditions for triggering a communication of an alert to an entity; receiving at least one additional user selection indicative of a change to the one or more displayed conditions for triggering the communication of an alert to an entity; and in response to receiving the at least one additional user selection, updating the selected alert rule.

In some embodiments, the alert modification interface further comprises at least one variable element configured to permit a user to modify information provided in the communication of an alert to an entity. In some embodiments, instructions for receiving at least one additional user selection indicative of a change to the one or more displayed conditions further comprise instructions configured to cause the processors to perform operations comprising: receiving at least one property associated with a value; and generating the value within the communication of an alert to an entity. In some embodiments the storage medium further comprises instructions configured to cause the processors to perform operations comprising: determining whether a calculation request matches the one or more conditions for triggering the communication, wherein in response to a determination that a calculation request matches the one or more conditions for triggering the communication, including the alert in the communication to the entity; and in response to a determination that a calculation request does not match the one or more conditions for triggering the communication, forgoing including the alert in the communication to the entity. In some embodiments, at least one alert rule of the one or more alert rules is associated with a priority level with respect to the one or more alert rules. In some embodiments, the entity is a patient and the communication is associated with health care information. In some embodiments, instructions for displaying one or more alert rules further comprise instructions configured to cause the processors to perform operations comprising: displaying, on the display, a preview of a communication of an alert to an entity, wherein the preview of a communication of alert to an entity corresponds to a currently selected alert rule.

In some embodiments, the present invention includes a system for updating an alert rule, the system comprising: a display; one or more processors; and a memory storing one or more programs, wherein the one or more programs include instructions configured to be executed by the one or more processors, causing the one or more processors to perform operations comprising: displaying, on a display, one or more alert rules; receiving a first user selection of a displayed alert rule; in response to receiving the user selection, displaying, on the display, an alert modification interface corresponding to the selected alert rule, wherein the alert modification interface includes one or more conditions for triggering a communication of an alert to an entity; receiving at least one additional user selection indicative of a change to the one or more displayed conditions for triggering the communication of an alert to an entity; and in response to receiving the at least one additional user selection, updating the selected alert rule.

In some embodiments, the alert modification interface further comprises at least one variable element configured to permit a user to modify information provided in the communication of an alert to an entity. In some embodiments, instructions for receiving at least one additional user selection indicative of a change to the one or more displayed conditions further comprise instructions configured to cause the processors to perform operations comprising: receiving at least one property associated with a value; and generating the value within the communication of an alert to an entity. In some embodiments the storage medium further comprises instructions configured to cause the processors to perform operations comprising: determining whether a calculation request matches the one or more conditions for triggering the communication, wherein in response to a determination that a calculation request matches the one or more conditions for triggering the communication, including the alert in the communication to the entity; and in response to a determination that a calculation request does not match the one or more conditions for triggering the communication, forgoing including the alert in the communication to the entity. In some embodiments, at least one alert rule of the one or more alert rules is associated with a priority level with respect to the one or more alert rules. In some embodiments, the entity is a patient and the communication is associated with health care information. In some embodiments, instructions for displaying one or more alert rules further comprise instructions configured to cause the processors to perform operations comprising: displaying, on the display, a preview of a communication of an alert to an entity, wherein the preview of a communication of alert to an entity corresponds to a currently selected alert rule.

DETAILED DESCRIPTION

In general, the invention provides for an alert rule system and method for updating alert rules. Furthermore, the present invention may take the form of an entirely software embodiment, entirely hardware embodiment, or a combination of software and hardware embodiments. Even further, the present invention may take the form of a computer program product contained on a computer-readable storage medium, where computer-readable code is embodied on the storage medium. In another embodiment, the present invention may take the form of computer software implemented as a service (SaaS). Any appropriate storage medium may be utilized, such as optical storage, magnetic storage, hard disks, or CD-ROMs.

In the following description of the disclosure and examples, reference is made to the accompanying drawings in which it is shown by way of illustration specific examples that can be practiced. It is to be understood that other examples can be practiced and structural changes can be made without departing from the scope of the disclosure.

The embodiments of the disclosure can be used to define (e.g., by administrators or internal users of the system of the disclosure) and/or implement (e.g., while generating communications to be transmitted to end users of the system, such as patients, healthcare providers, their staff, the general public, etc.) one or more alert rules (e.g., in some embodiments, with varying priorities and/or trigger conditions) to match against a request for communication with an entity in order to provide real time and dynamically updating sets of alerts for that entity. For example, an end user (e.g., a patient) can access a website (e.g., a healthcare provider's website) to view or request a communication from the system (e.g., a request for an estimated cost of a procedure)—each time the patient visits the website to view or request the communication from the system, the system can reevaluate alert rules that are relevant to the patient's communication (e.g., alerts that communicate information about the patient's insurance relevant to the requested estimate, such as conditions on when the insurance will cover the procedure, information required before being able to determine whether the insurance will cover the procedure, an indication that the estimate is a low-confidence or high-confidence estimate, information about steps the patient must take before the insurance company will pay for the procedure, etc.) to refresh the information included in the communication resulting from those alert rules. In this way, hardcoded rules or alerts associated with that given communication can be avoided; rather, the alerts displayed (or not) with the communication can be dynamic. Thus, the embodiments of the disclosure allow for automated and efficient communications with entities, which the prior art cannot achieve (e.g., the embodiments of the disclosure allow for dynamic alert rules and corresponding communications, which can be evaluated at each communication request, whereas the prior art does not)—as such, the embodiments of the disclosure provide a technology-based solution to the technological problem presented by communicating alerts between entities that must take into account large amounts of information and constraints, and do so in a dynamic manner. It is understood that the communications of the disclosure can be associated with different types of information, such as healthcare information, healthcare pricing information, healthcare pricing estimates information, etc.

Figure 1:
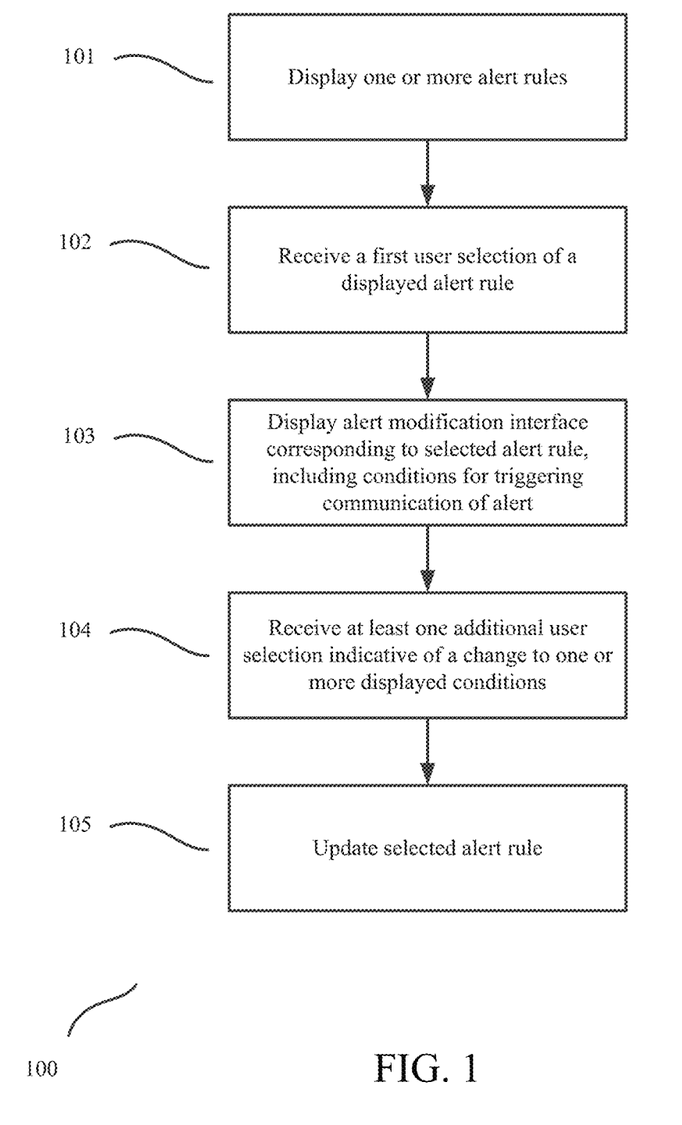
FIG. 1 illustrates an exemplary process for updating an alert rule.

FIG. 1 illustrates an exemplary process 100 for updating an alert rule (e.g., as may be performed by a system administrator or internal user of the system). In one embodiment, process 100 may begin at step 101 by displaying one or more alert rules. Alert rules may correspond to conditions configured to trigger the communication of an alert to at least one entity (e.g., a patient). Such alerts are further described with respect to FIG. 2. Furthermore, for example, an alert may be displayed concurrently with an estimate, as discussed further with respect to FIG. 3B. The communication of the alert to an entity may include communication to entities such as patients, physicians, technicians, administrators, or other entities receiving such communications as described herein, such as estimates for services, requests for information, and the like. However, the communication of alerts is not limited to such entities. In some embodiments, communications can be any information meant to be transmitted to another entity (e.g., a patient, a healthcare provider, etc.) in any manner, such as e-mail communications, SMS communications, postal communications, telephone communications, internet communications (e.g., communications displayed on a website requested by the other entity), etc.

Figure 2:
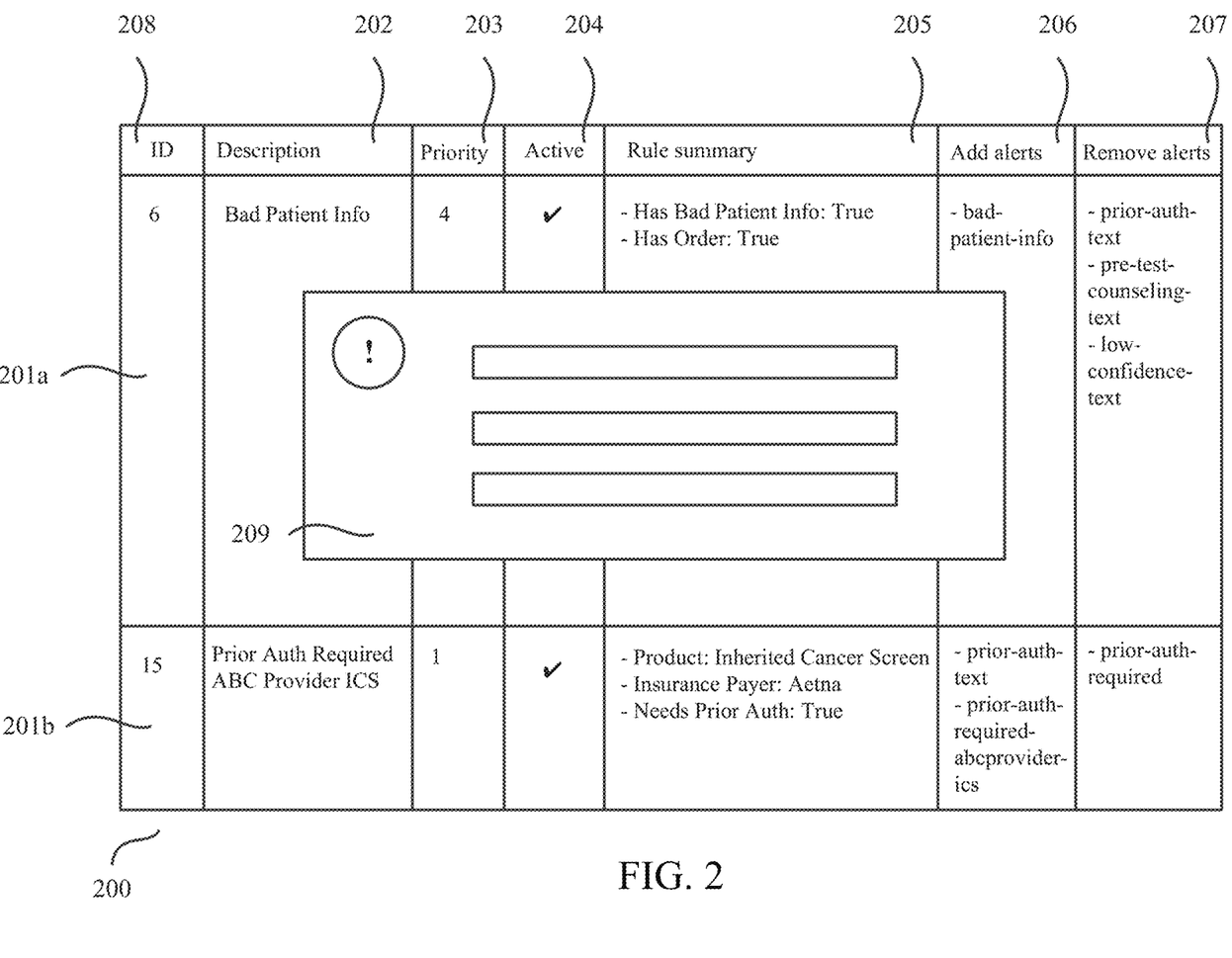
FIG. 2 illustrates an exemplary user interface for selecting an alert rule from one or more displayed alert rules.

FIG. 2 illustrates an exemplary user interface 200 for selecting an alert rule from one or more displayed alert rules. As shown in FIG. 2, a pricing estimate alert rule user interface 200 is displayed, where one or more alert rules 201 may be displayed within the user interface. In one embodiment, one or more alert rules may include an identification (ID) 208, which may individually identify a given alert rule. Alert rules 201 may further include, for example, a description 202 which may briefly identify the alert rule and summarize attributes or characteristics of the alert rule. For example, alert rule 201a may include a description 202 for "Bad Patient Information," which may be associated with a condition where a system does not have sufficient information to provide the patient with an accurate estimate for a given service or services, as described herein. As another example, alert rule 201b may include a description 202 for "Prior Auth Required," which may be associated with a condition where authorization from a patient's insurance company is required.

The rule summary 205 and associated types of rules will now be described. In one embodiment, a rule summary 205 may summarize a corresponding alert rule. For example, each alert rule may include at least one condition that is used to trigger a communication of an alert to a user. As shown in FIG. 2, alert rule 201a may be associated with rule summaries 205 corresponding to conditions for "Bad Patient Information" and "Has Order." In one embodiment, as described above, a "Bad Patient Information" rule summary 205 may be associated with a condition such that the system does not have sufficient information to provide the patient with an accurate estimate for a given service or services, such as when insurance information is missing or not stored in the system for a respective patient. For example, "Bad Patient Information" may apply to a situation where manual research regarding insurance information is necessary. In one embodiment, a "Has Order" rule summary 205 may be associated with a condition such that an estimate corresponds to an order which has been converted in the system from a first type to a second type. For example, an order which has not been converted in the system from a first type to a second type may include orders such as an electronic medical record request by an administrator or clinical staff. In one embodiment, each condition may be associated with a qualifier, such as true or false. For example, alert rule 201a is optionally triggered (e.g., and, thus, the alerts 206 associated with alert rule 201a are included in the communication) in response to both the "Has Bad Patient Info" and the "Has Order" conditions being true. In some embodiments, alert rules 201 are associated with alerts to be removed from the communication 207 if the alert rule is triggered. For example, if alert rule 201a is triggered, "prior-auth-text", "pre-test-counseling text" and "low-confidence text" are all optionally removed from the communication.

As further shown in FIG. 2, alert rules 201 may be associated with additional rule summaries 205 corresponding to one or more conditions. For example, alert rule 201b may be associated with a rule summary 205 corresponding to "Product," "Insurance Payer," and "Needs Prior Auth" conditions. In one embodiment, a rule summary 205 for a "Product" condition may identify one or more specific types of tests that the alert rule applies to. For example, specific types of tests may include a family preparation screening test, a pregnancy screening test, or an inherited cancer screening test, as described further herein. However, the one or more specific types of tests may include additional types of tests. In one embodiment, where a rule summary 205 for a "Product" condition is not included within an alert rule, any number of specific types of tests from a given list of tests may match the respective alert rule. In one embodiment, a rule summary 205 for an "Insurance Payer" condition may identify an insurer that a claim will be filed to. In one embodiment, as described above, a rule summary 205 for the "Needs Prior Auth" condition may be associated with a scenario where a patient's insurance company requires authorization for a given procedure contained in the patient's order. In one embodiment, conditions may be dependent on any number of other conditions. For example, the "Needs Prior Auth" condition may be set to "false" if a patient's bill type does not correspond to insurance, or if the patient does not meet a coverage criteria, which may be defined by another condition.

Although FIG. 2 depicts specific rule summaries 205 associated with alert rules 201a and 201b, FIG. 2 is provided for exemplary purposes only, such that any combination of conditions and corresponding rule summaries 205 may be used, as described herein. Accordingly, alert rules 201 may correspond to additional rule summaries 205 and associated conditions not depicted in FIG. 2. Further, in some embodiments, conditions for triggering rules 201 (e.g., as reflected in rule summaries 205) can be Boolean conditions, number/inequality conditions (e.g., greater than a quantity, less than a quantity, equal to a quantity), character string conditions (e.g., includes a particular character string, such as "Aetna"), other entity/object conditions (e.g., associated with a particular insurer, account network status, etc.), and in some embodiments, these conditions can be combined in different manners, such as AND (all conditions need to be satisfied to trigger a particular alert), OR (at least one condition needs to be satisfied to trigger a particular alert) or grouped (e.g., a first group of the conditions is combined with AND while a second group of the conditions is combined with OR). For example, in one embodiment, alert rules 201 may correspond to a "Benefits Administrator" condition, which may define an organization administering benefits and applying a policy, similar to or the same as the "Insurance Payer" condition. As one example, the "Benefits Administrator" condition may differ from the "Insurance Payer" condition for a third-party administrated plan. In one embodiment, alert rules 201 may correspond to a "Payer Family" condition, which may define a family of an insurer, such as, for example, Medicaid. In one embodiment, alert rules 201 may correspond to an "In Network" condition, which may define whether a respective insurer has accepted a discounted rate (e.g., in-network rate) or has not accepted a discounted rate (e.g., out-of-network rate) for a given claim.

Furthermore, in one embodiment, alert rules 201 may correspond to a "Plan Type" condition, which may define an insurance plan type for a given patient. For example, insurance plan types may include, but are not limited to, a PPO (Preferred Provider Organization), HMO (Health Maintenance Organization), POS (Point of Service), EPO (Exclusive Provider Organization), HDHP (High Deductible Health Plan), Indemnity, Medicare Part A (Hospital), Medicare Part B (Professional Services), Medicare Part C (Advantage), or Medicare Part D (Secondary). In one embodiment, alert rules 201 may correspond to a "Plan Name" condition, which may identify an insurance plan name for a given patient. In one embodiment, alert rules 201 may correspond to a "Plan Comments" condition, which may identify insurance plan comments from an eligibility response. In one embodiment, alert rules 201 may correspond to an "Applied OPR Discount to Estimate" condition, which may identify a subtraction to the estimate based on an administrator policy, such as a policy not to bill patients under certain scenarios. In one embodiment, alert rules 201 may correspond to a "Billing Policy" condition which corresponds to a bill type, such as claims that are required to be filed or claims that are unable to be filed. For example, the "Billing Policy" condition may refer to a billing policy for a claim, or alternatively, to a billing policy on an estimate. In one embodiment, a billing policy for a claim may take precedence over a billing policy on an estimate. In one embodiment, alert rule 201 may correspond to a "Patient-visible Bill Type" condition, which may define whether the bill type, such as insurance or self-pay, is visible to a user.

Furthermore, in one embodiment, alert rules 201 may correspond to a "Coverage Has Expired" condition, which may be associated with a scenario where a respective patient's insurance coverage has expired based on stored information regarding the patient's insurance policy. In one embodiment, alert rules 201 may correspond to a "Coverage Expires Soon" condition, which may be associated with a scenario where a respective patient's insurance coverage is expected to expire within a predetermined time. For example, the predetermined time may be set by an administrator or other user, and correspond to 2 weeks, 30 days, 60 days, or another value. In one embodiment, alert rules 201 may correspond to a "Meets Medical Criteria" condition, which may be associated with a scenario where an administrator has determined that a respective patient will meet one or more predetermined medical criteria for an ordered test. For example, predetermined criteria may correspond to the patient having a high risk indication, or a family history indication associated with a type of disease or other test subject. In one embodiment, alert rules 201 may correspond to a "Claim Is Invoiced" condition, which may be associated with a scenario where an insurance claim has previously been invoiced to a respective patient. In one embodiment, alert rules 201 may correspond to a "Claim Is Filed" condition, which may be associated with a scenario where an insurance claim has previously been filed to a respective insurer. In one embodiment, alert rules 201 may correspond to a "Claim Active Tags" condition, which may be associated with a scenario where an insurance claim has been previously tagged for one or more individualized reasons, such as prior authorization being denied. In one embodiment, alert rules 201 may correspond to a "Claim Historical Tags" condition, which may be associated with a scenario where an insurance claim has been previously tagged for one or more reasons, and the tag was subsequently removed, such that the claim is no longer tagged.

In one embodiment, alert rules 201 may include an "Active" field 204, which may be a Boolean value or other value to signify whether the alert rule is active or inactive in the system. In one embodiment, alert rules 201 may each include a priority value 203, such that numerically higher priority alert rules can override lower priority alert rules. For example, where a "Bad Patient Information" condition would apply, but a higher priority rule regarding claim coverage also applies, the "Bad Patent Information" condition may be ignored or partially ignored in order to account for the rule regarding claim coverage. In other words, in some embodiments, higher-priority alert rules can override or replace lower-priority alert rules (e.g., such that if a lower-priority alert rule and a higher-priority alert rule are both triggered, the higher-priority alert rule can control to the extent that the two alert rules conflict with one another). However, to the extent that the alert rules do not conflict with one another, they can supplement one another (e.g., the non-conflicting results of the alert rules can be implemented). In one embodiment, alert rules 201 may be associated with one or more add alerts 206 and one or more remove alerts 207. For example, as discussed with respect to FIG. 3, add alerts 206 may correspond to preconfigured text which will be communicated to an entity in an alert, when corresponding conditions for a given alert rule 201 are triggered. For example, add alert 206 for "bad-patient-info" may correspond to alert text such as "We do not have your correct information on file and cannot provide you with an estimate of your out-of-pocket cost with your insurance." Furthermore, remove alerts 207 may correspond to preconfigured text which will not be communicated to an entity in an alert, when corresponding conditions for a given alert rule 201 are triggered. For example, where a first alert rule 201 includes a higher priority value 203 than a second alert rule 201, add alerts 206 and remove alerts 207 for the first alert rule 201 may control or partially control, whereas add alerts 206 and remove alerts 207 for the second alert rule 201 may be ignored or partially ignored. In one embodiment, an alert sample 209 may be generated for a currently selected alert rule 201, which may be representative of an alert to be communicated to an entity for the given conditions of the selected alert rule 201. For example, the alert sample 209 may be associated with a full preview of the associated alert communication, or a partial preview of the associated alert communication, and displayed on the user interface.

Referring back to FIG. 1, process 100 may continue with the receiving of a first user selection of a displayed alert rule at step 102. For example, a user may utilize an input device or other input process to select one of the displayed alert rules 201 depicted in FIG. 2. In one example, upon selection of a displayed alert rule 201 by the user, the selected alert rule 201 may displayed to indicate that the alert rule 201 has been selected, such as rendering the selected alert rule in a highlighted or grayed-out appearance. In one embodiment, selection of a displayed alert rule may cause an alert modification interface to be generated and displayed on a display screen at step 103, as further discussed in FIG. 3.

Figure 3A:
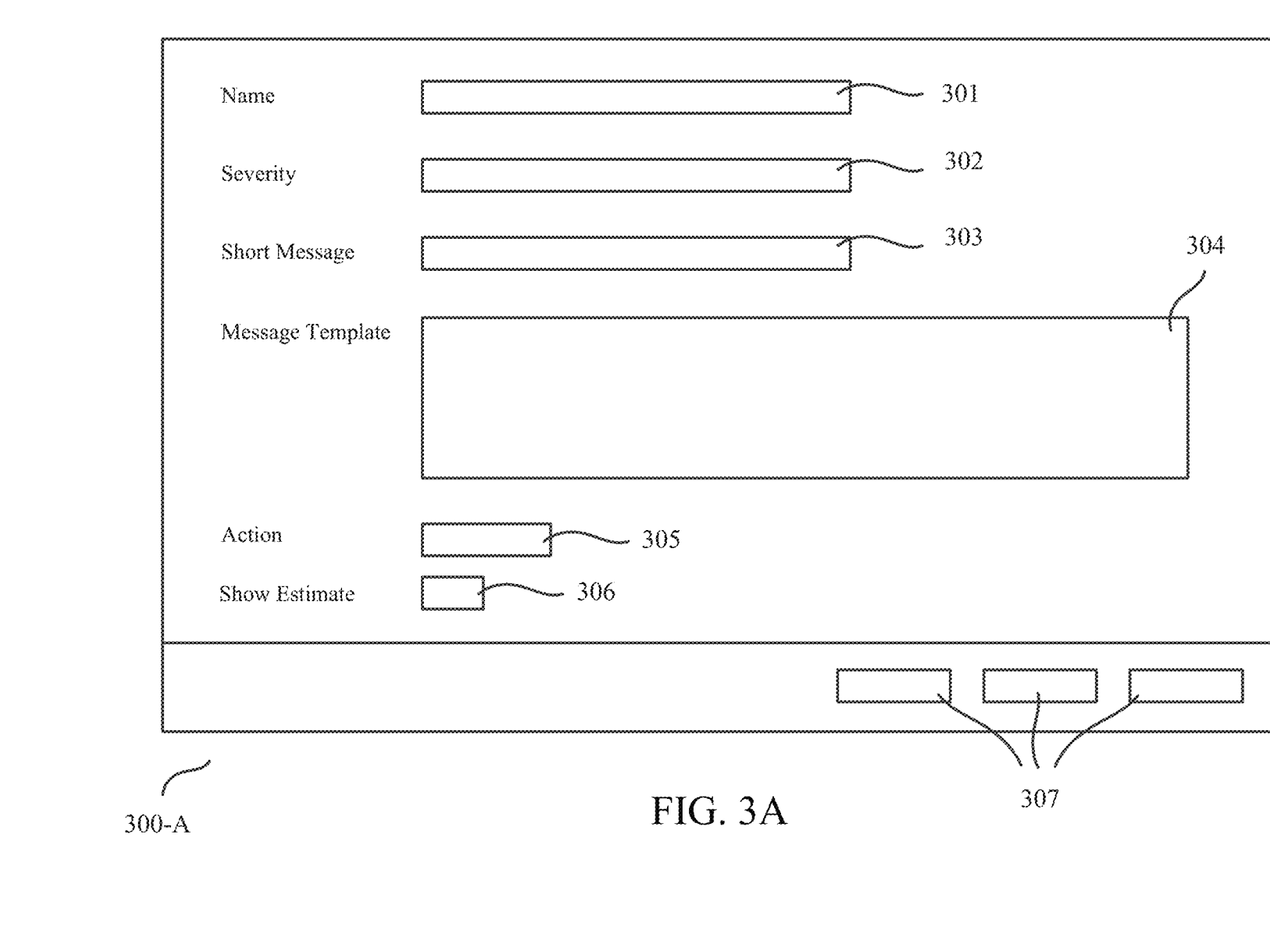
FIG. 3A illustrates an exemplary alert modification interface for changing an alert notification.
Figure 3B:
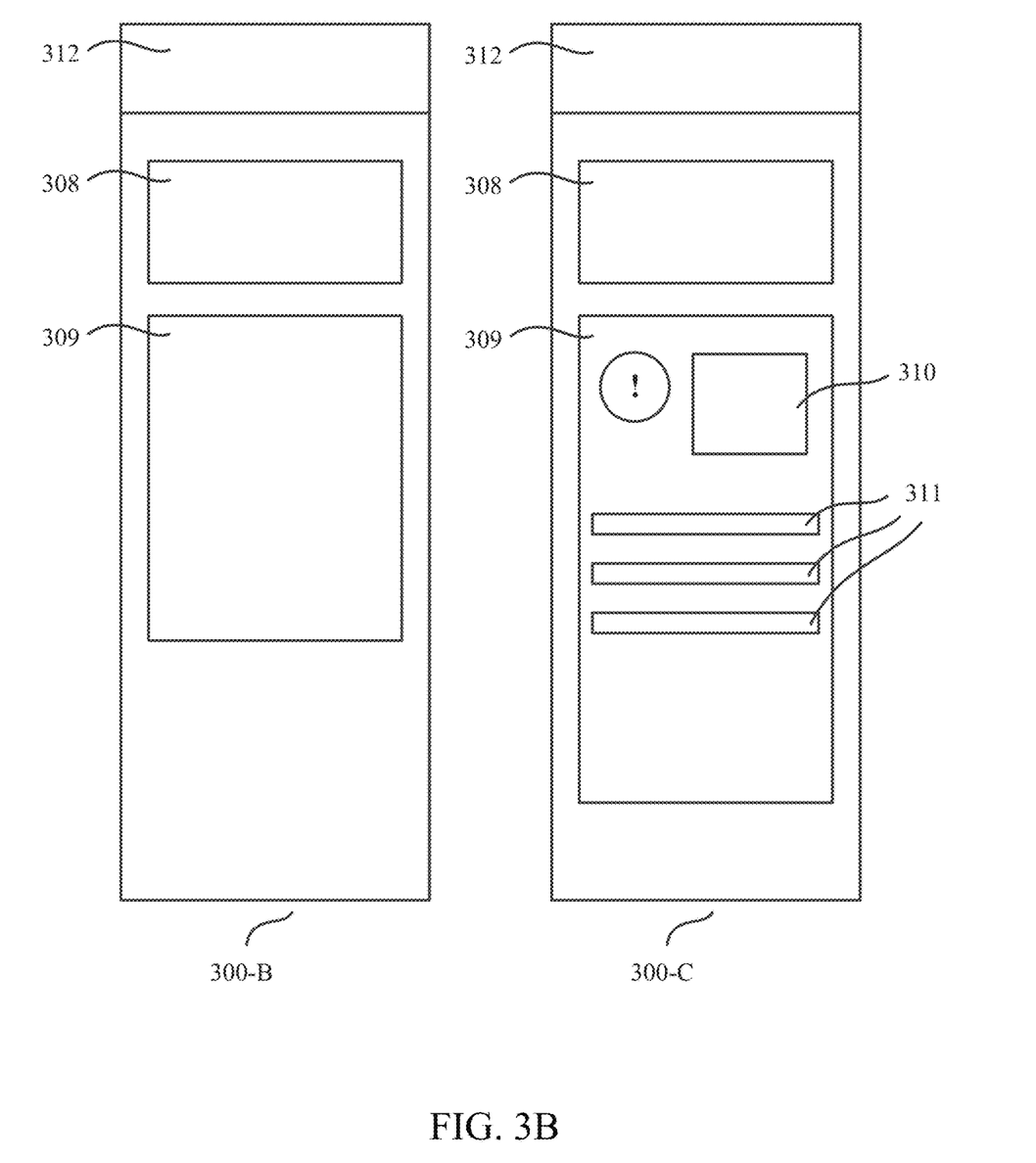
FIG. 3B illustrates exemplary user interfaces for notification communications.

FIG. 3A illustrates an exemplary alert modification interface 300-A for changing an alert notification. In one embodiment, alert modification interface 300-A may be configured as an administrative tool in order to modify one or more parameters, values, conditions, rules, logic, and other elements associated with a selected alert rule. Furthermore, alert modification interface 300-A may permit a user to modify the content and appearance of an alert notification, such as the content and appearance of exemplary notifications 300-B and 300-C as depicted in FIG. 3B. In one embodiment, alert notifications may be communicated to an entity based on the modified parameters, values, conditions, rule, logic, and other elements. Upon display of alert modification interface 300-A, one or more variable elements 301-306 pertaining to the selected alert rule may be displayed on the display screen. For example, an alert rule name 301 may be displayed, which may correspond to a short reference for a given alert. In one embodiment, the alert rule name 301 may correspond to the one or more add alerts 206 and remove alerts 207 depicted in FIG. 2. Alert rule name 301 may, for example, be customizable by a user, such that the alert rule name 301 may be represented by a text string or other identifier. In one embodiment, in order to customize a given alert rule, a user may select alert rule name 301, and input one or more characters to represent the alert rule, such as "prior-auth-required."

FIG. 3B illustrates exemplary user interfaces for notification communications (e.g., communications transmitted to an entity, such as a patient). In one embodiment, notification 300-B may be associated with a notification to an entity, wherein the notification does not include the communication of an alert to the entity (e.g., because no alert rules were triggered). In one embodiment, alert notification 300-C may be associated with a notification which includes the communication of an alert to an entity (e.g., the one or more alert rules for which triggering conditions were met). In one embodiment, each of notification 300-B and alert notification 300-C may be associated with one or more informational elements. In one embodiment, notification 300-B and alert notification 300-C may each include a header informational element 312, such as an entity name, logo, slogan, or the like. In one embodiment, notification 300-B and alert notification 300-C may each include a summary informational element 308. In one embodiment, notification 300-B and alert notification 300-C may each include a details informational element 309. In one embodiment, details element 309 of alert notification 300-C may further include an introductory message element 310 and a details message element 311 (e.g., which are optionally not included in notification 300-B).

Referring back to FIG. 1, process 100 may continue with the receiving of at least one additional user selection indicative of a change to one or more displayed conditions at step 104. The additional user selections may correspond to user customization of alert rules as described herein. With reference to FIG. 3A, in one embodiment, short message element 303 may, for example, be customizable by a user, such that the short message may represented by a text string or other identifier. In one embodiment, in order to customize a given short message, a user may select short message element 303, and enter one or more characters to represent the short message, such as "Your insurance requires prior authorization for this test." Contents within the short message element 303 may correspond to the introductory message element 310 of alert notification 300-C for the selected alert rule, for example. In one embodiment, message template element 304 may, for example, be customizable by a user, such that the short message may represented by a text string or other identifier. In one embodiment, in order to customize a given message template, a user may select message template element 304, and enter one or more characters to represent the message template, such as "This test requires prior authorization from your insurance company. Company will work with your provider to submit prior authorization on your behalf. There's no action required by you, but the following estimated cost with insurance may change if prior authorization is denied. If denied, you will automatically receive our self-pay price of {{currency cash_price}}." Contents within the message template element 304 may correspond to the details message element 311 of alert notification 300-C in FIG. 3B for the selected alert rule, for example.

In one embodiment, the user may utilize one or more properties and associated property categories in order to customize message template 304, as described further herein. For example, a "{{currency cash_price}}" property may be associated with a stored system value within an estimate and price information category, where the stored system value includes a self-pay price based on one or more conditions associated with a respective order, a respective entity receiving the communication, and other relevant factors and/or conditions. In one embodiment, some properties utilized within message template element 304 may be, such that the properties may vary based on other associated properties, whereas some properties utilized within message template element 304 may be static, such that the properties remain constant regardless of the conditions in which the alert message is communicated to an entity. In one embodiment, utilization of "{{currency cash_price}}" within message template element 304 will result in a value of "$349.00," being communicated to an entity within the details message element 311 of alert notification 300-C in FIG. 3B, based on at least the stored system value including a self-pay price, which is associated with the "{{currency cash_price}}" property. Accordingly, the message communicated to an entity within details message element 311 may read "This test requires prior authorization from your insurance company. Company will work with your provider to submit prior authorization on your behalf. There's no action required by you, but the following estimated cost with insurance may change if prior authorization is denied. If denied, you will automatically receive our self-pay price of $349.00." The user customization of the message template may include the utilization of any number of properties for creating an alert notification tailored to a specific entity receiving the alert notification.

In one embodiment, alert rule severity 302 may define the importance or severity level of an alert based on how the alert is presented to the user. In one embodiment, alert rule severity 302 may define an appearance of the alert communication to a user, such as an alert notification 300-C as depicted in FIG. 3C. For example, a user may customize an alert rule severity 302 to be associated with a "Warning" level. When presented with a "Warning" level, an alert communicated to a user may be provided in a specific color, such as in yellow accents with a yellow background. In one embodiment, a "Warning" level may be associated with a condition where prior authorization is required before further processing can commence, for example. As another example, a user may customize an alert rule severity 302 to be associated with an "Error" level. In one embodiment, an "Error" level may be associated with a condition where the user must update insurance information before further processing can commence, for example. When presented with an "Error" level, an alert communicated to a user may be provided in a specific color, such as in red accents with a yellow background. As another example, a user may customize an alert rule severity 302 to be associated with an "Info" level. In one embodiment, an "Info" level may be associated with a condition where the user is being presented with information regarding an ongoing process, such as the insurance claim processing has completed, for example. When presented with an "Info" level, an alert communicated to a user may be provided in a specific color, such in as green accents with a yellow background. Furthermore, any combination of appearances and associated severity levels may be utilized, such that the appearance and associated rule severity levels are not limited to those described herein.

In one embodiment, with reference to FIG. 3A, the alert modification interface 300-A may further include an "Action" element 305, which may be configured to communicate one or more action items to a user within an alert message. In one embodiment, a user may select at least one of a plurality of actions of which to communicate to an entity, such as "Update Insurance Information." Referring back to FIG. 3B, a selected action corresponding to "Action" element 305 may be communicated in an entity details message element 311 of alert notification 300-C. Furthermore, for example, the communicated action may include one or more variable elements for an entity to interact with, such as a button or "check-box" in order to permit the user to signify a choice regarding the communicated action. In one embodiment, alert modification interface 300-A may further include a "Show Estimate" element 306, which may be configured to permit or forgo communication of estimate details to an entity. For example, a user may toggle "Show Estimate" element 306 between an on or off state, whereby respective details regarding an estimate, such as a "{{currency cash_price}}" property, would be shown or omitted from a communication, respectively. Alert modification interface 300-A may further includes one or more options 307 for saving details associated with a currently displayed alert rule. The one or more options 307 may include, for example, a "Save and Add Another" option, which if activated, may save a current alert rule and generate a new alert modification interface 300-A for creating a new alert rule. The one or more options 307 may further include, for example, a "Save and Continue Editing" option, which if activated, may save a current alert rule and permit a user to continue editing a respective alert rule within alert modification interface 300-A. The one or more options 307 may further include, for example, a "Save" option, which if activated, may save a current alert rule and exit the alert modification interface 300-A. Referring back to FIG. 1, in response to receiving at least one additional user selection indicative of a change to one or more displayed conditions, a selected alert rule may be updated at step 105. In one embodiment, utilization of the one or more options 307 as depicted in FIG. 3A may correspond to the updating of a selected alert rule at step 105 in FIG. 1.

Figure 4:
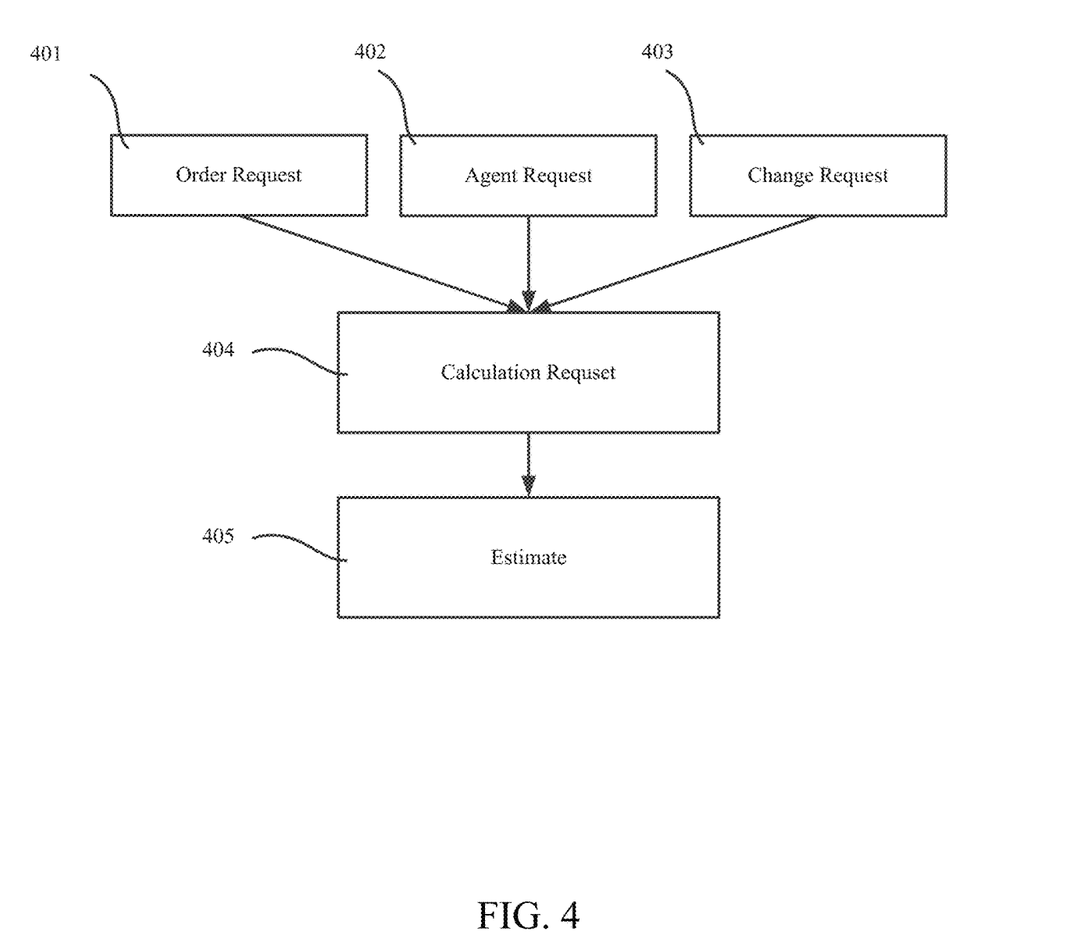
FIG. 4 illustrates an exemplary process for providing an estimate in response to one or more requests.

FIG. 4 illustrates an exemplary process 400 for providing an estimate in response to one or more requests. In one embodiment, process 400 may begin at any of steps 401, 402, or 403. In one embodiment, process 400 may begin at step 401, where an order request is generated. For example, generation of an order request at 401 may occur when a paper medical record or electronic medical record is processed and an order and corresponding insurance claim is generated. As another example, an order request may be generated at 401 when an entity visits a service provider and the service provider submits a primary order on behalf of the entity, triggering the order request generation. For example, a service provider may include a health care provider, diagnostic service provider, or any other service provider associated with the generation of an order and processing of order estimates, whereas an entity may include a consumer, customer, or other entity capable of requesting an order and receiving a corresponding estimate. However, a service provider and entity are not limited as such.

In one embodiment, process 400 may begin with the generation of an agent request at step 402. For example, generation of an agent request at step 402 may occur when a service provider or agent of an entity provides entity information into an order request service, such as a web form or physical form. In one embodiment, process 400 may begin with the generation of a change request at step 403. For example, generation of a change request at step 403 may occur when an entity requests a change to an existing order, such as a patient requesting a change through a web form or a clinic requesting a change through an administrative process. Generation of a change request may, for example, further invoke the generation of an insurance claim.

In one embodiment, in response to at least one of an order request 401, agent request 402, and a change request 403, a calculation request 404 may be generated (e.g., a request corresponding to a communication to be generated, and triggering application of the alert rules of the disclosure). In one embodiment, generation of a calculation request 404 may include the accessing of stored data that represents a request to create an estimate, such as a pricing estimate for a specific service. For example, the stored data may include data necessary to formulate an estimate, such as data associated with an entity. Such data may include, but is not limited, to demographics (e.g., a patient demographic), insurance information, and billing information. In one embodiment, generation of a calculation request 404 may include the accessing of a previously saved estimate. Referring back to FIG. 2, one or more conditions of a given alert rule 201 may match one or more elements of a generated calculation request 404. In one embodiment, where all conditions of a given alert rule 201 match one or more elements of a generated calculation request at step 404, an estimate may be generated at step 405 including corresponding alert information as described herein. For example, alert notification 300-C as described in FIG. 3B may be generated with appropriate alerts based on the matched conditions of the alert rule and calculation request. In one embodiment, where conditions of a given alert rule 201 do not match the elements of a generated calculation request at step 404, an estimate may be generated at step 405 without corresponding alert information as described herein. For example, alert notification 300-B as described in FIG. 3 may be generated in accordance with standard or routine procedures where no match is found between the conditions of the alert rule and calculation request. Further, as described herein, generation of the estimate at 405 can be associated with different alert rules for the initial communication/estimate and subsequent communications/estimates for the same calculation request. Specifically, the alert rules in effect for the initial estimate can be different than the alert rules in effect for subsequent estimates (e.g., because administrators have changed the alert rules); the triggering conditions for the alert rules in effect for the initial estimate can be different than the triggering conditions for the alert rules in effect for subsequent estimates (e.g., because administrators have changed the alert rule conditions); the triggered alert rules for the initial estimate can be different than the triggered alert rules for the subsequent estimates (e.g., because the evaluated factors that trigger/don't trigger the alert rule conditions can have changed since the initial estimate—for example, the patient's insurance information could have changed); etc. More generally, because the alert rules of the disclosure can be evaluated dynamically at each communication generation, the outcome of that evaluation can be different at each communication generation.

As discussed with respect to FIG. 3A, one or more properties and associated property categories may be utilized in customizing alert rules. For example, property categories for use in alert messages may include, but are not limited to, related objects, patient and insurance information, order information, benefits information, estimate and price information, and billing information. The related object category may include properties such as insurance claims, price calculator requests, pricing estimates, and code sets. The patient and insurance information category may include properties such as first name, last name, gender, date of birth, member identification, group number, payer name, and benefits administrator name. The order information category may include properties such as product, product name, product description, disease panel, clinic name, physician first name, physician last name, creation date, CPT codes, microdeletions, and turn-around time. The benefits information category may include properties such as plan end date, coverage expiration, and yearly deductible. The estimate and price information category may include properties such as low confidence, benefit coverage, cash price, total charges, list price, estimated insurance discount, estimated total out-of-pocket, estimated total out-of-pocket before computation, estimated total out-of-pocket lower bound, estimated total out-of-pocket before computation lower bound, raw estimated total out-of-pocket, estimated deductible, estimated coinsurance percent, estimated coinsurance, estimated copayment, and estimated other patient responsibility.

In one embodiment, as described with respect to FIG. 2 above, a family preparation screening test may include screening for conditions including, but not limited to, 21-hydroxylase-deficient Congenital Adrenal Hyperplasia, ABCC8-related Hyperinsulinism, Achondrogenesis Type 1B, Achromatopsia, Alkaptonuria, Alpha Thalassemia, Alpha-1 Antitrypsin Deficiency, Alpha-mannosidosis, Alpha-sarcoglycanopathy, Andermann Syndrome, ARSACS, Aspartylglycosaminuria, Ataxia with Vitamin E Deficiency, Ataxia-telangiectasia, Bardet-Biedl Syndrome (BBS1-related), Bardet-Biedl Syndrome (BBS10-related), Beta-sarcoglycanopathy, Biotinidase Deficiency, Bloom Syndrome, Canavan Disease, Carnitine Palmitoyltransferase IA Deficiency, Carnitine Palmitoyltransferase II Deficiency, Cartilage-hair Hypoplasia, Choroideremia, Citrullinemia Type 1, CLN3-related Neuronal Ceroid Lipofuscinosis, CLN5-related Neuronal Ceroid Lipofuscinosis, Cohen Syndrome, Congenital Disorder of Glycosylation Type Ia, Congenital Disorder of Glycosylation Type Ib, Congenital Finnish Nephrosis, Costeff Optic Atrophy Syndrome, Cystic Fibrosis, Cystinosis, D-bifunctional Protein Deficiency, Diastrophic Dysplasia, Dihydropyrimidine Dehydrogenase Deficiency, Factor V Leiden Thrombophilia, Factor XI Deficiency, Familial Dysautonomia, Familial Mediterranean Fever, Fanconi Anemia Type C, FKTN-related Disorders, Fragile X Syndrome, Galactosemia, Gaucher Disease, GJB2-related DFNB1 Nonsyndromic Hearing Loss and Deafness, Glucose-6-phosphate Dehydrogenase Deficiency, Glutaric Acidemia Type 1, Glycogen Storage Disease Type Ia, Glycogen Storage Disease Type Ib, Glycogen Storage Disease Type III, Glycogen Storage Disease Type V, GRACILE Syndrome, HADHA-related Disorders, Hb Beta Chain-related Hemoglobinopathy (Including Beta Thalassemia and Sickle Cell Disease), Hereditary Fructose Intolerance, Herlitz Junctional Epidermolysis Bullosa, LAMA3-related, Herlitz Junctional Epidermolysis Bullosa, LAMB3-related, Herlitz Junctional Epidermolysis Bullosa, LAMC2-related, Hexosaminidase A Deficiency (Including Tay-Sachs Disease), FIFE-associated Hereditary Hemochromatosis, Homocystinuria Caused by Cystathionine Beta-synthase Deficiency, Hypophosphatasia, Autosomal Recessive, Inclusion Body Myopathy 2, Isovaleric Acidemia, Joubert Syndrome 2, Krabbe Disease, Lipoamide Dehydrogenase Deficiency, Maple Syrup Urine Disease Type 1B, Medium Chain Acyl-CoA Dehydrogenase Deficiency, Megalencephalic Leukoencephalopathy with Subcortical Cysts, Metachromatic Leukodystrophy, Mild Hyperhomocysteinemia Caused by MTHFR Deficiency, Mucolipidosis IV, Mucopolysaccharidosis Type I, Muscle-eye-brain Disease, NEB-related Nemaline Myopathy, Niemann-Pick Disease Type C, Niemann-Pick Disease, SMPD1-associated, Nijmegen Breakage Syndrome, Northern Epilepsy, PCDH15-related Disorders, Pendred Syndrome, PEX1-related Zellweger Syndrome Spectrum, Phenylalanine Hydroxylase Deficiency, PKHD1-related Autosomal Recessive Polycystic Kidney Disease, Polyglandular Autoimmune Syndrome Type 1, Pompe Disease, PPT1-related Neuronal Ceroid Lipofuscinosis, Primary Carnitine Deficiency, Primary Hyperoxaluria Type 1, Primary Hyperoxaluria Type 2, PROP1-related Combined Pituser interfacetary Hormone Deficiency, Prothrombin Thrombophilia, Pseudocholinesterase Deficiency, Pycnodysostosis, Recessive Multiple Epiphyseal Dysplasia, Rhizomelic Chondrodysplasia Punctata Type 1, Salla Disease, Segawa Syndrome, Short Chain Acyl-CoA Dehydrogenase Deficiency, Sjogren-Larsson Syndrome, Smith-Lemli-Opitz Syndrome, Spinal Muscular Atrophy, Steroid-resistant Nephrotic Syndrome, Sulfate Transporter-related Osteochondrodysplasia, TPP1-related Neuronal Ceroid Lipofuscinosis, Tyrosinemia Type I, Usher Syndrome Type 3, Very Long Chain Acyl-CoA, Dehydrogenase Deficiency, Wilson Disease, and/or X-linked Juvenile Retinoschisis.

In one embodiment, as described with respect to FIG. 2 above, a pregnancy screening test may include screening for conditions including, but not limited to, Trisomy 21 (Down syndrome), Trisomy 18 (Edwards syndrome), Trisomy 13 (Patau syndrome), Monosomy X (Turner syndrome), XXY Klinefelter syndrome, Trisomy X (Triple X syndrome), XYY Jacob syndrome, 22q11.2 deletion syndrome, 1p36 deletion syndrome, 15q11.2 deletion syndrome, 5p deletion (Cri du chat syndrome), and/or 4p deletion (Wolf-Hirschhorn syndrome).

In one embodiment, as described with respect to FIG. 2 above, an inherited cancer screening test may include screening genes for associated syndromes including, but not limited to, Familial adenomatous polyposis, ATM-associated hereditary cancer, Juvenile polyposis, BRCA-related breast and ovarian cancer syndrome, BRIP1-associated hereditary cancer, Hereditary diffuse gastric cancer, Familial Atypical Multiple Mole Melanoma (FAMMM) syndrome, CHEK2-associated hereditary cancer, Lynch syndrome, Hereditary mixed polyposis syndrome (HMPS), MUTYH-associated polyposis, PALB2-associated hereditary cancer, Lynch syndrome, Polymerase proofreading associated polyposis (PPAP) syndrome, PTEN hamartoma tumor syndrome, RAD51C-associated hereditary cancer, RAD51D-associated hereditary cancer, Multiple endocrine neoplasia type 2, Juvenile polyposis, Peutz-Jeghers, Li-Fraumeni syndrome, Von Hippel-Lindau, BARD1-associated hereditary cancer, Multiple endocrine neoplasia type 1, MRE11A-associated hereditary cancer, NBN-associated hereditary cancer, RAD50-associated hereditary cancer, and/or Hereditary paraganglioma-pheochromocytoma.

Figure 5:
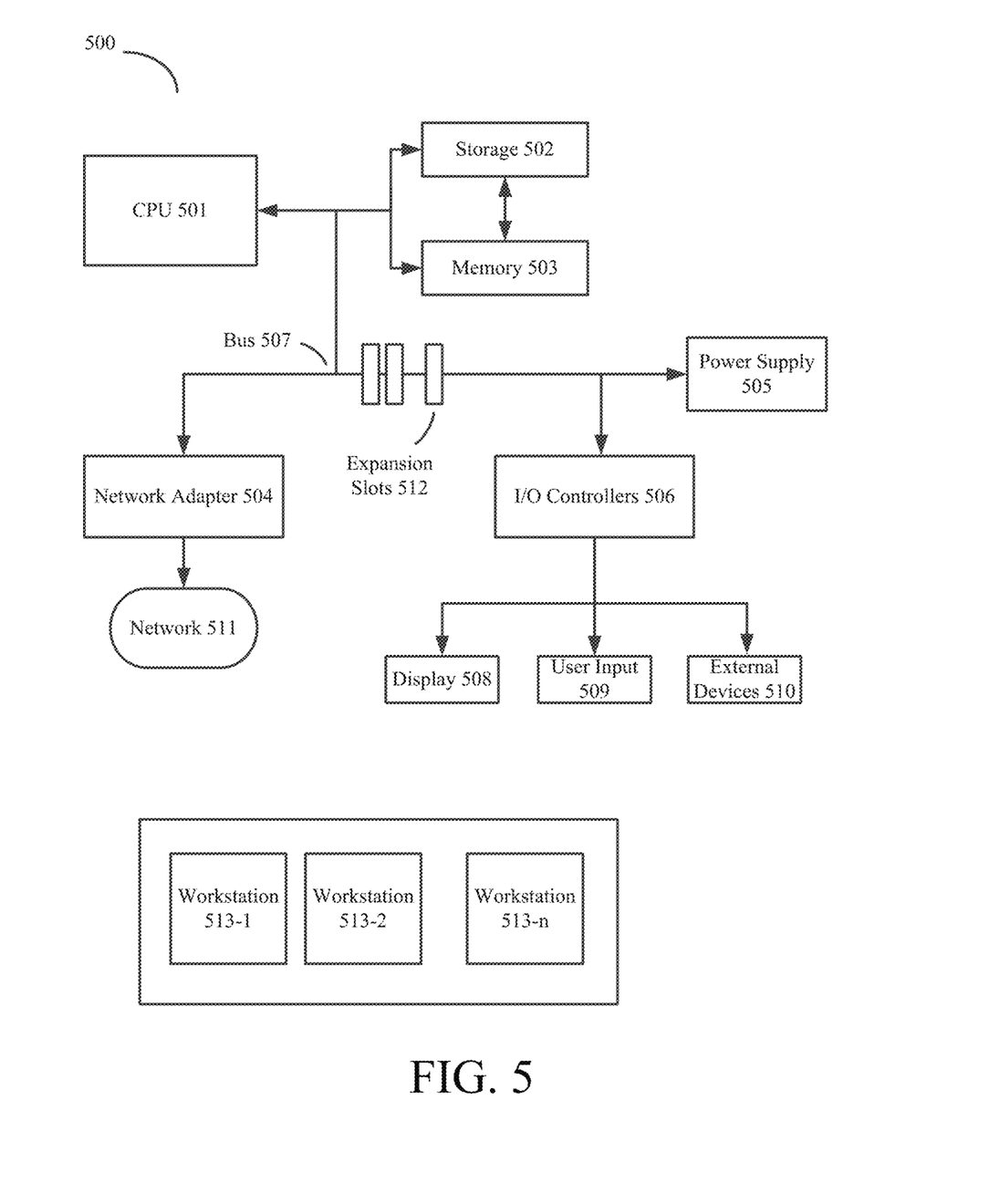
FIG. 5 illustrates a general purpose computing system in which one or more systems of the present invention may be implemented.

FIG. 5 illustrates a general purpose computing system 500 in which one or more systems, as described herein, may be implemented. System 500 may include, but is not limited to known components such as central processing unit (CPU) 501, storage 502, memory 503, network adapter 504, power supply 505, input/output (I/O) controllers 506, electrical bus 507, one or more displays 508, one or more user input devices 509, and other external devices 510. It will be understood by those skilled in the art that system 500 may contain other well-known components which may be added, for example, via expansion slots 512, or by any other method known to those skilled in the art. Such components may include, but are not limited to, hardware redundancy components (e.g., dual power supplies or data backup units), cooling components (e.g., fans or water-based cooling systems), additional memory and processing hardware, and the like.

System 500 may be, for example, in the form of a client-server computer capable of connecting to and/or facilitating the operation of a plurality of workstations or similar computer systems over a network. In another embodiment, system 500 may connect to one or more workstations over an intranet or internet network, and thus facilitate communication with a larger number of workstations or similar computer systems. Even further, system 500 may include, for example, a main workstation or main general purpose computer to permit a user to interact directly with a central server. Alternatively, the user may interact with system 500 via one or more remote or local workstations 513. As will be appreciated by one of ordinary skill in the art, there may be any practical number of remote workstations for communicating with system 500.

CPU 501 may include one or more processors, for example Intel® Core™ i7 processors, AMD FX™ Series processors, or other processors as will be understood by those skilled in the art. CPU 501 may further communicate with an operating system, such as Windows NT® operating system by Microsoft Corporation, Linux operating system, or a Unix-like operating system. However, one of ordinary skill in the art will appreciate that similar operating systems may also be utilized. Storage 502 may include one or more types of storage, as is known to one of ordinary skill in the art, such as a hard disk drive (HDD), solid state drive (SSD), hybrid drives, and the like. In one example, storage 502 is utilized to persistently retain data for long-term storage. Memory 503 may include one or more types of memory as is known to one of ordinary skill in the art, such as random access memory (RAM), read-only memory (ROM), hard disk or tape, optical memory, or removable hard disk drive. Memory 503 may be utilized for short-term memory access, such as, for example, loading software applications or handling temporary system processes.

As will be appreciated by one of ordinary skill in the art, storage 502 and/or memory 503 may store one or more computer software programs. Such computer software programs may include logic, code, and/or other instructions to enable processor 501 to perform the tasks, operations, and other functions as described herein, and additional tasks and functions as would be appreciated by one of ordinary skill in the art (e.g., the one or more central processing units ("CPU") 501 can execute the stored one or more computer programs (or instructions) to perform the above-described processes). Operating system 502 may further function in cooperation with firmware, as is well known in the art, to enable processor 501 to coordinate and execute various functions and computer software programs as described herein. Such firmware may reside within storage 502 and/or memory 503.

Moreover, I/O controllers 506 may include one or more devices for receiving, transmitting, processing, and/or interpreting information from an external source, as is known by one of ordinary skill in the art. In one embodiment, I/O controllers 506 may include functionality to facilitate connection to one or more user devices 509, such as one or more keyboards, mice, microphones, trackpads, touchpads, or the like. For example, I/O controllers 506 may include a serial bus controller, universal serial bus (USB) controller, FireWire controller, and the like, for connection to any appropriate user device. I/O controllers 506 may also permit communication with one or more wireless devices via technology such as, for example, near-field communication (NFC) or Bluetooth™. In one embodiment, I/O controllers 506 may include circuitry or other functionality for connection to other external devices 510 such as modem cards, network interface cards, sound cards, printing devices, external display devices, or the like. Furthermore, I/O controllers 506 may include controllers for a variety of display devices 508 known to those of ordinary skill in the art. Such display devices may convey information visually to a user or users in the form of pixels, and such pixels may be logically arranged on a display device in order to permit a user to perceive information rendered on the display device. Such display devices may be in the form of a touch-screen device, traditional non-touch screen display device, or any other form of display device as will be appreciated be one of ordinary skill in the art.

Furthermore, CPU 501 may further communicate with I/O controllers 506 for rendering a graphical UI (user interface) on, for example, one or more display devices 508. In one example, CPU 501 may access storage 502 and/or memory 503 to execute one or more software programs and/or components to allow a user to interact with the system as described herein. In one embodiment, a UI as described herein includes one or more icons or other graphical elements with which a user may interact and perform various functions. For example, UI may be displayed on a touch screen display device 508, whereby the user interacts with the UI via the touch screen by physically contacting the screen with, for example, the user's fingers. As another example, UI may be displayed on a traditional non-touch display, whereby the user interacts with the UI via keyboard, mouse, and other conventional I/O components 509. The UI may reside in storage 502 and/or memory 503, at least in part as a set of software instructions, as will be appreciated by one of ordinary skill in the art. Moreover, the UI is not limited to the methods of interaction as described above, as one of ordinary skill in the art may appreciate any variety of means for interacting with a UI, such as voice-based or other disability-based methods of interaction with a computing system.

Moreover, network adapter 504 may permit device 500 to communicate with network 511. Network adapter 504 may be a network interface controller, such as a network adapter, network interface card, LAN adapter, or the like. As will be appreciated by one of ordinary skill in the art, network adapter 504 may permit communication with one or more networks 511, such as, for example, a local area network (LAN), metropolitan area network (MAN), wide area network (WAN), cloud network (IAN), or the Internet.

One or more workstations 513 may include, for example, known components such as a CPU, storage, memory, network adapter, power supply, I/O controllers, electrical bus, one or more displays, one or more user input devices, and other external devices. Such components may be the same, similar, or comparable to those described with respect to system 500 above. It will be understood by those skilled in the art that one or more workstations 513 may contain other well-known components, including but not limited to hardware redundancy components, cooling components, additional memory/processing hardware, and the like.

As used herein, the terminology as used throughout the description of the invention is for the purpose of describing particular embodiments only. Such terminology does not limit the scope of the invention in any way. For example, singular forms of "a," "an" and "the" are intended to include plural forms unless indicated otherwise. Furthermore, terms such as "comprises" or "comprising" specify the presence of indicated features, components, steps, etc., but do not preclude the presence or addition of one or more other features, components, steps, etc. The description may also include the term "in," which may include "in" and "on" unless clearly indicated otherwise. Furthermore, usage of the term "or" includes both conjunctive and disjunctive meanings, unless clearly indicated otherwise. That is, unless expressly stated otherwise, the term "or" may include "and/or."

It will be further understood that various modifications to the invention may be made by one skilled in the art without departing from the spirit and scope of the invention as defined in the claims. For example, numerous changes, substitutions, and variations with respect to the systems and methods as described may occur. One of ordinary skill in the art will understand that various alternative embodiments may be employed to practice the invention, and that any feature may be combined with any other feature, whether such features are preferred or not.

What is claimed is:

1. A computer-implemented method comprising:
displaying, on a display, a plurality of alert rules;
receiving a first user selection of a first alert rule displayed on the display;
in response to receiving the first user selection, displaying, on the display, an alert modification interface corresponding to the first alert rule, wherein the alert modification interface includes one or more conditions for triggering a communication of an alert to a first patient;
receiving at least one additional user selection indicative of a change to the one or more displayed conditions for triggering the communication of the alert to the first patient;
in response to receiving the at least one additional user selection, updating the first alert rule by at least updating a priority of the first alert rule;
receiving patient information from a plurality of different healthcare providers, wherein the patient information comprises names, billing information, and healthcare plans of a plurality of patients including the first patient;
processing the patient information through a processing system where the alert rules are implemented;
identifying the first patient, billing information of the first patient, and a healthcare plan of the first patient from the patient information;
receiving a request for a cost associated with a procedure;
determining, in response to receiving the request, that the first alert rule and a second alert rule in the plurality of alert rules are triggered;
determining that the patient information of the first patient is sufficient to generate an estimate of the cost associated with the procedure;
responsive to determining that the patient information of the first patient is sufficient to generate the estimate, generating, based in part on the billing information and the healthcare plan of the first patient, an estimate of the cost associated with the procedure and an indication of whether the estimate of the cost is a low-confidence or high-confidence estimate;
via the selected one or more alert rules, generating the alert with the estimate for the first patient and, according to the selected one or more alert rules, the indication of whether the estimate of the cost is a low-confidence or high-confidence estimate, wherein when the estimate is a low-confidence estimate, the estimate is removed from the alert; and
automatically communicating the alert to the first patient, wherein the alert modification interface further comprises at least one variable element configured to permit a user to input a text string in the communication of the alert to the first patient.

2. The method of claim 1, wherein receiving the at least one additional user selection indicative of the change to the one or more displayed conditions further comprises:
receiving at least one property associated with a value; and
generating the value within the communication of the alert to the first patient.

3. The method of claim 1, further comprising:
determining whether a calculation request matches the one or more conditions for triggering the communication, wherein in response to a determination that the calculation request matches the one or more conditions for triggering the communication, including the alert in the communication to the first patient; and
in response to a determination that a calculation request does not match the one or more conditions for triggering the communication, forgoing including the alert in the communication to the first patient.

4. The method of claim 1, wherein displaying the plurality of alert rules further comprises:
displaying, on the display, a preview of a communication of the alert to the first patient, wherein the preview of the communication of the alert to the first patient corresponds to the selected alert rule.

5. The method of claim 1, further comprising:
at a first time, in response to receiving a request for a first communication of a first type, evaluating the plurality of alert rules and including corresponding information from a first set of the plurality of alert rules in the first communication of the first type; and
at a second time, different than the first time, in response to receiving a request for a second communication of the first type, evaluating the plurality of alert rules and including corresponding information from a second set of the plurality of alert rules, different than the first set of the plurality of alert rules, in the second communication of the first type.

6. A non-transitory computer readable storage medium having instructions stored thereon, the instructions, when executed by one or more processors, cause the processors to perform operations comprising:
displaying, on a display, a plurality of alert rules;
receiving a first user selection of a first alert rule displayed on the display;
in response to receiving the first user selection, displaying, on the display, an alert modification interface corresponding to the first alert rule, wherein the alert modification interface includes one or more conditions for triggering a communication of an alert to a first patient;
receiving at least one additional user selection indicative of a change to the one or more displayed conditions for triggering the communication of the alert to the first patient;

in response to receiving the at least one additional user selection, updating the first alert rule by at least updating a priority of the first alert rule;

receiving a third user selection indicative of an action item to be communicated to the first patient with an interactive element to permit the first patient to interact with the alert with respect to the action item;

in response to receiving the third user selection, updating the first alert rule by at least updating an action element of the first alert rule;

receiving patient information from a plurality of different healthcare providers, wherein the patient information comprises names, billing information, and healthcare plans of a plurality of patients including the first patient;

processing the patient information through a processing system where the alert rules are implemented;

identifying the first patient, billing information of the first patient, and a healthcare plan of the first patient from the patient information;

receiving a request for a cost associated with a procedure;

determining, in response to receiving the request, that the first alert rule and a second alert rule in the plurality of alert rules are triggered;

determining either that (i) the first alert rule conflicts with the second alert rule and consequently selecting either the first alert rule or the second alert rule according to corresponding priorities of the first alert rule and the second alert rule, or otherwise that (ii) the first alert rule does not conflict with the second alert rule and consequently selecting both the first alert rule and the second alert rule;

determining that the patient information of the first patient is sufficient to generate an estimate of the cost associated with the procedure;

responsive to that the patient information of the first patient is sufficient to generate the estimate, generating, based in part on the billing information and the healthcare plan of the first patient, an estimate of the cost associated with the procedure and an indication of whether the estimate of the cost is a low-confidence or high-confidence estimate, wherein when the estimate is a low-confidence estimate, the estimate is removed from the alert;

via the selected one or more alert rules, generating the alert with the estimate and the action item for the first patient, the alert comprising, according to the selected one or more alert rules, an indication of the confidence level in the estimate of the cost; and automatically communicating the alert with the interactive element to the first patient, wherein the alert modification interface further comprises at least one variable element configured to permit a user to input a text string in the communication of the alert to the first patient.

7. The storage medium of claim 6, wherein instructions for receiving at least one additional user selection indicative of the change to the one or more displayed conditions further comprise instructions configured to cause the processors to perform operations comprising:

receiving at least one property associated with a value; and generating the value within the communication of the alert to the first patient.

8. The storage medium of claim 6, further comprising instructions configured to cause the processors to perform operations comprising:

determining whether a calculation request matches the one or more conditions for triggering the communication, wherein in response to a determination that the calculation request matches the one or more conditions for triggering the communication, including the alert in the communication to the first patient; and in response to a determination that a calculation request does not match the one or more conditions for triggering the communication, forgoing including the alert in the communication to the first patient.

9. The storage medium of claim 6, wherein instructions for displaying the plurality of alert rules further comprise instructions configured to cause the processors to perform operations comprising:

displaying, on the display, a preview of a communication of the alert to the first patient, wherein the preview of the communication of the alert to the first patient corresponds to the selected alert rule.

10. The storage medium of claim 6, further comprising instructions configured to cause the processors to perform operations comprising:

at a first time, in response to receiving a request for a first communication of a first type, evaluating the plurality of alert rules and including corresponding information from a first set of the plurality of alert rules in the first communication of the first type; and at a second time, different than the first time, in response to receiving a request for a second communication of the first type, evaluating the plurality of alert rules and including corresponding information from a second set of the plurality of alert rules, different than the first set of the plurality of alert rules, in the second communication of the first type.

11. A system comprising:

a display;

one or more processors; and a memory storing one or more programs, wherein the one or more programs include instructions configured to be executed by the one or more processors, causing the one or more processors to perform operations comprising:

displaying, on a display, a plurality of alert rules;

receiving a first user selection of a first alert rule displayed on the display;

in response to receiving the first user selection, displaying, on the display, an alert modification interface corresponding to the first alert rule, wherein the alert modification interface includes one or more conditions for triggering a communication of an alert to a first patient;

receiving at least one additional user selection indicative of a change to the one or more displayed conditions for triggering the communication of the alert to the first patient;

in response to receiving the at least one additional user selection, updating the first alert rule by at least updating a priority of the first alert rule;

receiving a third user selection indicative of an action item to be communicated to the first patient with one or more interactive elements in the alert to permit the first patient to interact with the alert with respect to the action item;

in response to receiving the third user selection, updating the first alert rule by at least updating an action element of the first alert rule;

receiving patient information from a plurality of different healthcare providers, wherein the patient information comprises names, billing information, and healthcare plans of a plurality of patients including the first patient;

processing the patient information through a processing system where the alert rules are implemented;

identifying the first patient, billing information of the first patient, and a healthcare plan of the first patient from the patient information;

receiving a request for a cost associated with a procedure;

determining, in response to receiving the request, that the first alert rule and a second alert rule in the plurality of alert rules are triggered;

determining either that (i) the first alert rule conflicts with the second alert rule and consequently selecting either the first alert rule or the second alert rule according to corresponding priorities of the first alert rule and the second alert rule, or otherwise that (ii) the first alert rule does not conflict with the second alert rule and consequently selecting both the first alert rule and the second alert rule;

determining that the patient information of the first patient is sufficient to generate an estimate of the cost associated with the procedure;

responsive to determining that the patient information of the first patient is sufficient to generate the estimate, generating, based in part on the healthcare plan of the first patient, an estimate of the cost associated with the procedure and an indication of whether the estimate of the cost is a low-confidence or high-confidence estimate, wherein when the estimate is a low-confidence estimate, the estimate is removed from the alert;

via the selected one or more alert rules, generating the alert with the estimate and the action item for the first patient, the alert comprising, according to the selected one or more alert rules, an indication of the confidence level in the estimate of the cost; and automatically communicating the alert with the one or more interactive elements to the first patient, wherein the alert modification interface further comprises at least one variable element configured to permit a user to input a text string in the communication of the alert to the first patient.

12. The system of claim 11, wherein instructions for receiving at least one additional user selection indicative of the change to the one or more displayed conditions further comprise instructions configured to cause the processors to perform operations comprising:

receiving at least one property associated with a value; and generating the value within the communication of the alert to the first patient.

13. The system of claim 11, further comprising instructions configured to cause the processors to perform operations comprising:

determining whether a calculation request matches the one or more conditions for triggering the communication, wherein in response to a determination that the calculation request matches the one or more conditions for triggering the communication, including the alert in the communication to the first patient; and in response to a determination that a calculation request does not match the one or more conditions for triggering the communication, forgoing including the alert in the communication to the first patient.

14. The system of claim 11, wherein instructions for displaying the plurality of alert rules further comprise instructions configured to cause the processors to perform operations comprising:

displaying, on the display, a preview of a communication of the alert to the first patient, wherein the preview of the communication of the alert to the first patient corresponds to the selected alert rule.

15. The system of claim 11, further comprising instructions configured to cause the processors to perform operations comprising:

at a first time, in response to receiving a request for a first communication of a first type, evaluating the plurality of alert rules and including corresponding information from a first set of the plurality of alert rules in the first communication of the first type; and at a second time, different than the first time, in response to receiving a request for a second communication of the first type, evaluating the plurality of alert rules and including corresponding information from a second set of the plurality of alert rules, different than the first set of the plurality of alert rules, in the second communication of the first type.

16. The method of claim 1, wherein the patient information is billing or healthcare plan information of the first patient, and wherein the alert comprises an interactive element that is configured to permit the first patient to interact with the alert to signify a choice with respect to an action item.

17. The method of claim 1, further comprising:

receiving a third user selection indicative of an action item to be communicated to the first patient with one or more interactive elements configured to permit the first patient to interact with the alert with respect to the action item; and in response to receiving the third user selection, updating the selected alert rule by at least updating an action element of the selected alert rule.

18. The method of claim 17, wherein the alert is communicated with an interactive element that comprises at least one of a button or a check-box to permit the first patient to signify a choice with respect to the action item.

19. The method of claim 1, wherein the request for the cost associated with the procedure is received via a website accessible to the first patient for viewing or requesting communications.

* * * * *